United States Patent
Slavin

(10) Patent No.: US 8,494,638 B2
(45) Date of Patent: Jul. 23, 2013

(54) CERVICAL SPINAL CORD STIMULATION FOR THE TREATMENT AND PREVENTION OF CEREBRAL VASOSPASM

(75) Inventor: Konstantin V. Slavin, Oak Park, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 612 days.

(21) Appl. No.: 12/510,848

(22) Filed: Jul. 28, 2009

(65) Prior Publication Data
US 2010/0042193 A1  Feb. 18, 2010

Related U.S. Application Data

(60) Provisional application No. 61/054,909, filed on Jul. 28, 2008.

(51) Int. Cl.
*A61N 1/00* (2006.01)
(52) U.S. Cl.
USPC .............................. 607/45; 607/46
(58) Field of Classification Search
USPC ........................................... 607/45–46
See application file for complete search history.

(56) References Cited

U.S. PATENT DOCUMENTS

| | | | |
|---|---|---|---|
| 6,058,331 A | 5/2000 | King | |
| 7,286,879 B2 | 10/2007 | Wallace | |
| 7,340,298 B1 | 3/2008 | Barbut | |
| 2006/0047325 A1* | 3/2006 | Thimineur et al. | 607/45 |
| 2006/0058854 A1* | 3/2006 | Abrams et al. | 607/45 |
| 2006/0193893 A1 | 8/2006 | Brown | |
| 2007/0032864 A1 | 2/2007 | Furst et al. | |
| 2007/0060954 A1 | 3/2007 | Cameron et al. | |
| 2007/0083245 A1 | 4/2007 | Lamensdorf et al. | |
| 2008/0021503 A1 | 1/2008 | Whitehurst et al. | |
| 2008/0208284 A1 | 8/2008 | Rezai et al. | |
| 2009/0105783 A1 | 4/2009 | Solberg et al. | |
| 2009/0118780 A1 | 5/2009 | DiLorenzo | |

OTHER PUBLICATIONS

Burchiel et al., "Peripheral neuropathic pain syndromes," *Textbook of neurological surgery*, pp. 3013-3022 (2003).
Cetas et al., "Coupled control of pain and cerebral blood flow in the medulla," *New horizons in functional neurosurgery*, p. 81 (2008).
Clavo et al., Increased locoregional blood flow in brain tumors after cervical spinal cord stimulation, *J. Neurosurg.*, 98:1263-70 (2003).
Doberstein et al., "Cerebral blood flow in clinical neurosurgery," *Neurological*, 4: 519-69 (1996).
Ebel et al., "High cervical spinal cord stimulation (CSCS) increases regional cerebral blood flow after induced subarachnoid haemorrhage in rats," *Minim. Invasive Neurosurg.*, 44: 167-71 (2001).

(Continued)

*Primary Examiner* — Nicole F Lavert
(74) *Attorney, Agent, or Firm* — Marshall, Gerstein & Borun LLP

(57) ABSTRACT

The present invention relates to a method of prevention and treatment of narrowing of cerebral blood vessels after subarachnoid hemorrhage, and in particular, to a method of applying electrical energy through electrical stimulation electrodes particularly positioned in the cervical region of a patient to affect the sympathetic tone of the blood vessels supplying the brain.

14 Claims, 3 Drawing Sheets

OTHER PUBLICATIONS

Faleiros et al., "Effects of cervical sympathectomy on vasospasm induced by meningeal haemorrhage in rabbits," *Arq. Neuropsiquiatr.*, 64:572-4 (2006).

Fisher et al., "Relation of cerebral vasospasm to subarachnoid hemorrhage visulaized by computerized tomographic scanning," *Neurosurgery*, 6: 1-9 (1980).

Frontera et al., "Prediction of symptomatic vasospasm after subarachnoid hemorrhage: the modified fisher scale," *Neurosurgery*, 59: 21-7 (2006).

Goellner et al., "Cervical spinal cord stimulation may prevent cerebral vasospasm by modulating sympathetic activity of the superior cervical ganglion at lower cervical spinal level," *Medical Hypotheses*, 73:410-413 (2009).

Gurelik et al., "Cervical spinal cord stimulation improves neurological dysfunction induced by cerbral vasospasm," *Neuroscience*, 134: 827-32 (2005).

Hosobuchi, Y., "Electrical stimulation of the cervical spinal cord increases cerebral blood flow in humans," *Appl. Neurophysiol*, 48:372-6 (1985).

Hosobuchi, Y., "Treatment of cerebral ischemia with electrical stimulation of the cervical spinal cord," *Pacing Clin. Electrophysiol*, 14:122-6 (1991).

Isono et al., "Effect of spinal cord stimulation on cerebral blood flow in cats," *Stereotact Funct. Neurosurg.*, 64: 40-6 (1995).

Lee et al., "Effect of electrical stimulation of the cervical spinal cord on blood flow following subarachnoid hemorrhage," *J. Neurosurg.*, 109: 1148-54 (2008).

Macdonald et al., "Pathology and pathogenesis," *Cerebral vasospasm*, pp. 870174 (2001).

Mocco et al., "A review of current and future medical therapies for cerebral vasospasm following aneurismal subarachnoid hemorrhage," *Neurosurg. Focus*, 21(3): E9 (2006).

Naredi et al., "Increased sympathetic nervous activity in patients with nontraumatic subarachnoid hemorrhage," *Stroke*, 31:901-6 (2000).

Patel, S. et al., "Evidence for a central pathway in the cerebrovascular effects of spinal cord stimulation," *Neurosurgery*, 55:201-6 (2004).

Patel, S. et al., "Sympathetic mechanisms in cerebral blood flow alterations induced by spinal cord stimulation," *J. Neurosurg.*, 99:754-61 (2003).

Robaina et al., "Spinal cord stimulation in the treatment of post-stroke patients: current state and future directions," *Acta Neurochir*, 97:277-82 (2007).

Sagher O. et al., "Effects of cervical spinal cord stimulation on cerebral blood flow in the rat," *J. Neurosurg.*, 93:71-6 (2000).

Slavin, K., "Epidural spinal cord stimulation: indications and technique," *Handbook of functional and stereotactic surgery*, pp. 417-430 (2002).

Takanashi et al., "Spinal cord stimulation for cerebral vasospasm as prophylaxis," *Neurol. Med. Chir.*, 40:352-6 (2000).

Treggiari et al., "Cervical sympathetic block to reverse delayed ischemic neurological deficits after aneurysmal subarachnoid hemorrhage," *Stroke*, 34:961-7 (2003).

Truex et al., "Strong and Elwyn's human neuroanatomy," Baltimore: Williams & Wilkins, pp. 240-242 (1964).

Upadhyaya et al., "Cervical spinal cord stimulation in cerebral ischemia," *Acta. Neurochir.*, 97:267-75 (2007).

Vincenzo, S. et al., "Epidural spinal cord stimulation in lower limb ischemia," *Acta. Neurochir.*, 97:253-8 (2007).

Visocchi et al., "Spinal cord stimulation and cerebral blood flow: an experimental study," *Stereotact. Funct. Neurosurg.*, 62:186-90 (1994).

Visocchi et al., "Spinal cord stimulation and early experimental cerebral spasm: the "functional monitoring" and the "preventing effect,"" *Acta. Neurochir.*, 143:177-85 (2001).

Visocchi, M., "Spinal cord stimulation and cerebral haemodynamics," *Acta. Neurochir.*, 99:111-6 (2006).

Yang, X. et al., "Roles of dorsal column pathway and transient receptor potential vanilloid type 1 in augmentation of cerebral blood flow by upper cervical spinal cord stimulation in rats," *Neuroscience*, 152:950-8 (2008).

Yasargil, M.G., *Microneurosurgery*, vol. 1, p. 271 (1984).

\* cited by examiner

CERVICAL SPINAL CORD STIMULATION FOR THE TREATMENT AND PREVENTION OF CEREBRAL VASOSPASM

BACKGROUND OF THE INVENTION

Narrowing of cerebral blood vessels (NCBV) or cerebral vasospasm is a pathological condition that frequently develops after subarachnoid hemorrhage and leads to impairment of cerebral blood flow, cerebral oxygen delivery and subsequent cerebral ischemia and stoke. It affects up to 60% of patients with hemorrhage after rupture of intracranial aneurysms.

Cerebral vasospasm has a number of symptoms that develop gradually, including depressed level of consciousness, numbness, weakness, visual loss and increased intracranial pressure; it is usually detected by means of transcranial Doppler ultrasound and cerebral angiography. Current methods of treating cerebral vasospasm or its symptoms have been only partially successful and the approaches to prevent cerebral vasospasm so far have not been effective. Common treatments include so-called "triple H" therapy (hypertension, hypervolemia and hemodilution), intraarterial infusion of smooth muscle relaxants (papaverine, verapamil) and endovascular balloon angioplasty; prophylactic measures include calcium channel blocker administration (nimodipine). All these measures, however, do not eliminate the risks of cerebral ischemia and only marginally improve clinical outcome.

Cerebral vasospasm is a decrease in diameter of arterial vessels that supply the brain. Its frequency and to some extent severity appear to be directly related to the amount of blood in the subarachnoid space. It appears that such narrowing may, at least in the beginning, be sympathetically mediated and therefore, sympathetic blockade may theoretically prevent cerebral vasospasm development. Such blockade on systemic level, however, would be worsening the brain perfusion as it would result in lowering the patient's blood pressure.

Cerebral vasospasm typically develops between 1 and 21 days after subarachnoid hemorrhage. Therefore, all interventions to prevent and treat cerebral vasospasm preferably should be done within this timeframe.

Spinal cord stimulation (SCS) is an established modality that is widely used to treat all kinds of chronic pain, primarily neuropathic in origin. It has also been successfully used to treat most severe cases of peripheral vascular disease and intractable angina. In the latter two applications, SCS effect is not limited to pain relief but also results in vasodilatation, similar to previous experience with surgical sympathectomy.

Multiple animal experiments [7-14] have shown augmentation of cerebral blood flow (CBF) with cervical SCS. Level of stimulation seemed to have direct effect on the blood flow, with stimulation of upper levels (C1-3) generating higher flow values.

Isono et al. [9] postulated that CBF is increased from cervical SCS mainly through a central pathway. Using a cat model, they showed that CBF augmentation with cervical SCS is no longer observed after sectioning of the dorsal columns at the cervicomedullary junction. Later, Patel et al. [12] obtained the same results using rat model. The Patel group also showed lack of changes in CBF after resection of superior cervical ganglion while using SCS.

Visocchi [27] has demonstrated that SCS can either increase, decrease or has no effect in CBF. The difference correlated mainly with the stimulated level of the spinal cord. Thoracic stimulation had low effect and sometimes even decreased CBF. Cervical stimulation more frequently produced CBF augmentation (61%). In another article [28], Visocchi et al. found that vasoconstriction of carotid arteries with sympathetic trunk stimulation were attenuated by cervical SCS. In this experiment they used rabbit model to observe CBF changes with SCS alone, sympathetic trunk stimulation alone and simultaneous spinal cord and sympathetic trunk stimulation.

Patel et al. observed that increase in CBF with SCS is in direct relation with specific sympathetic receptors [11]. Their experiments demonstrated that either sympathetic ganglion blocker or a1-adrenergic receptor blocker can abolish the response to SCS, but the same result does not happen with α or β-adrenergic receptor blockers.

The use of spinal cord stimulation for the treatment for cerebral vasospasm after SAH with SCS has been tried in different animal models. Ebel et al. [7] found increased blood flow in rats with SAH and SCS compared to control groups. Visocchi et al. [29] described prevention of early vasospasm in rabbits treated with SCS after induced SAH.

Recently, Lee et al. [10] showed the vasodilatation effect of SCS in the basilar artery of rats 5 days after induction of SAH. Radiotracer studies, laser Doppler flowmetry and histologic photomicrographs were used to prove these changes in the delayed spasm.

The effect of SCS on CBF in humans was first described by Hosobuchi in 1985 [30]. He found that SCS at upper cervical levels can increase CBF. The same result was not found with stimulation of thoracic levels. Later, he tested cervical SCS for patients with symptomatic cerebral ischemia in three patients (one with anterior and two with posterior circulation occlusion) [17]. Although good results were obtained, further studies were needed to confirm its clinical application.

Takanashi and Shinonaga [19] published the only article found in the literature related to the use of SCS for cerebral vasospasm in humans. Ten SAH patients with secured cerebral aneurysm (Hunt Hess grade 2 to 4 and Fisher) were implanted with percutaneous epidural cervical leads (C1-2). The stimulation was continuous and started on day 5 (±1) post bleeding for 10 to 15 days. The results were analyzed by the amount of increment in CBF with Xenon computed tomography and cerebral angiography before and after stimulation. CBF was significantly increased in the distribution of the middle cerebral artery. Four patients presented with angiographic vasospasm and 3 were reported with clinical vasospasm. One patient died and the overall outcome was good or excellent in 7. No major adverse effect was attributed to the use of SCS. The data analysis correlated increase in CBF with SCS. The electrodes were positioned all the way up to C1-2, with the intention of reaching the highest degrees of CBF augmentation.

SUMMARY OF THE INVENTION

The present invention is based on the discovery that spinal cord stimulation can be used for purposes other than pain management. The present inventors have identified spinal cord stimulation for both the treatment and prevention of cerebral vasospasm.

For example, in one aspect, the invention provides a method of preventing cerebral vasospasm in a subject having had a subarachnoid hemorrhage, the method comprising providing an electrical impulse generator capable of generating a predetermined electrical signal, wherein the electrical impulse generator is operatively coupled to a stimulation lead having an implantable electrode portion, wherein the electrical impulse generator is arranged to deliver the predetermined electrical signal to the electrode portion; selecting an implant location adjacent a lower cervical spinal region; surgically implanting the stimulation lead and positioning the electrode portion of the stimulation lead in an area adjacent to the implant location with the electrode portion disposed behind the spinal cord in the lower cervical spinal region, such that the stimulation lead is positioned to deliver the predetermined electrical signal from the electrical impulse generator to the selected implant location; and activating the electrical impulse generator for a predetermined period of time to generate the predetermined electrical signal to prevent cerebral vasospasm in the subject.

In another aspect, the invention provides a method of treating cerebral vasospasm in a subject having had a subarachnoid hemorrhage, the method comprising providing an electrical impulse generator capable of generating a predetermined electrical signal, wherein the electrical impulse generator is operatively coupled to a stimulation lead having an implantable electrode portion, wherein the connector the electrical impulse generator is arranged to deliver the predetermined electrical signal to the electrode portion; selecting an implant location adjacent an upper cervical spinal region; surgically implanting the stimulation lead and positioning the electrode portion of the stimulation lead in an area adjacent to the implant location and positioning the electrode portion behind the spinal cord in the upper cervical spinal region, such that the stimulation lead is positioned to deliver the predetermined electrical signal from the electrical impulse generator to the selected implant region; and activating the electrical impulse generator for a predetermined period of time to generate the predetermined electrical signal to prevent cerebral vasospasm in the subject.

In yet another aspect, the invention provides a method of applying spinal cord stimulation in a subject having had a subarachnoid hemorrhage, the method comprising providing an electrical impulse generator capable of generating a predetermined electrical signal, wherein the electrical impulse generator is operatively coupled to a stimulation lead having an implantable electrode portion, wherein the connector the electrical impulse generator is arranged to direct the predetermined electrical signal toward the electrode portion; assessing whether the subject has a presence of a cerebral vasospasm or an absence of a cerebral vasospasm; selecting a first implant location in an upper cervical spinal region based on the presence of cerebral vasospasm, and selecting a second implant location in a lower cervical spinal region based on the absence of cerebral vasospasm; surgically implanting the stimulation lead and positioning the electrode portion of the stimulation lead in an area behind the spinal cord adjacent the selected first or second implant location, such that the stimulation lead is positioned to deliver the predetermined electrical signal from the electrical impulse generator to the selected first or second implant location; and activating the electrical impulse generator for a predetermined period of time to generate the predetermined electrical signal to treat or prevent cerebral vasospasm in the subject.

In another aspect, the invention provides a method of applying spinal cord stimulation in a subject having had a subarachnoid hemorrhage, the method comprising providing an electrical impulse generator capable of generating a desired electrical signal, the electrical impulse generator operatively coupled to an implantable electrode and arranged to send the desired electrical signal toward the electrode; providing the electrode with a plurality of contacts, including a first group of contacts and a second group of contacts; assessing whether the subject has a presence or an absence of a cerebral vasospasm; implanting the electrode in a selected area adjacent the spine with the first group of contacts disposed adjacent a first desired location adjacent an upper cervical spinal region of the subject, and with the second group of contacts disposed adjacent a lower cervical spinal region of the subject; and activating the electrical impulse generator to deliver the desired electrical signal to only the first group of contacts based on the presence of cerebral vasospasm and activating the electrical impulse generator to deliver the electrical signal to only the second group of contacts based on the absence of cerebral vasospasm.

The predetermined electrical signal should be supplied in an effective amount to treat (or prevent) cerebral vasospasm. As used herein "effective amount" is variable among subjects but generally corresponds within a rate range of approximately 2 to 1000 pulses per second, a pulse width range of approximately 10 to 500 milliseconds, an amplitude range of approximately up to 10 volts, and electrode polarity set in monopolar, bipolar, tripolar or more complex pattern.

In one embodiment, the methods described herein comprise performing a partial removal of ligamentum flavum at a removal location and implanting the stimulation lead through the removal location. In another embodiment, the methods described herein comprise performing a partial laminectomy and implanting the stimulation lead through the partial laminectomy.

In some embodiments, the methods described herein comprise selecting the implant location adjacent to vertebra(e) in the lower cervical spinal region. In one embodiment, the lower cervical spinal region comprises one or more vertebra(e) at levels C3-C7. In another embodiment, the lower cervical spinal region comprises one or more vertebra(e) at levels C3-C5.

In other embodiments, the methods described herein comprise selecting the implant location adjacent to vertebra(e) in the upper cervical spinal region. In one embodiment, the upper cervical spinal region comprises one or more vertebra(e) at levels C1-C4. In another embodiment, the upper cervical spinal region comprises one or more vertebra(e) at levels C1-C3.

In some embodiments, the methods described herein comprise arranging the electrical impulse generator to cause the predetermined electrical signal to have an impulse frequency within the range of 2-3,000 Hz. In other embodiments, the impulse frequency generated is selected from the group consisting of 2, 5, 25, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000 Hz or more or any range therebetween.

In some embodiments, the stimulation lead is inserted at a vertebral position below or at the level of T1/T2 into an epidural space and advanced in a superior direction, substantially parallel to a longitudinal direction of the epidural space, until the electrode portion reaches a desired position relative to the cervical segments of the spinal cord.

In some embodiments, an apparatus and method disclosed herein is used to electrically stimulate selected level of the spinal cord within the epidural space of a patient to at least decrease the sympathetic tone in the cranial region and produce focal vascular relaxation of cerebral arteries of a patient.

In some embodiments, an apparatus and method disclosed herein is for the prevention and treatment of arterial vasospasm following the subarachnoid hemorrhage through continuous stimulation of the cervical spinal cord.

In some embodiments, the spinal cord stimulation described herein is administered to a subject in need thereof for a period of time selected from the group consisting of 30 minutes, 1 hour, 2 hours, 3 hours, 4 hours, 6 hours, 8 hours, 12 hours, 24 hours, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or longer if warranted by the subject's condition.

DETAILED DESCRIPTION OF THE INVENTION

Cerebral vasospasm is a serious complication that occurs following an aneurysmal subarachnoid hemorrhage (SAH). Its presentation and demographics have already been established [1,2], but the complete understanding of its pathophysiology remains unclear. The aim of treatment usually is to maintain uninterrupted brain oxygenation using multimodality approaches [3,4].

Spinal cord stimulation (SCS) is an accepted method of treatment of chronic refractory pain due to central and peripheral problems [5,6]. The effects of cervical SCS on cerebral blood flow (CBF) are well known based on experimental investigations [7-14], and its vasodilatory effect on peripheral arteries is widely used in clinical settings in treatment of peripheral vascular disease [15]. Possible indications for the treatment of cerebrovascular conditions and brain tumors are now under investigation with initial results appearing quite promising [16-20].

The inventors have discovered that the location of SCS along the axis of the cervical spinal cord correlates with the prophylactic and therapeutic effects of this modality on cerebral vasculature, specifically on management of the SAH related arterial vasospasm.

Figure 1:
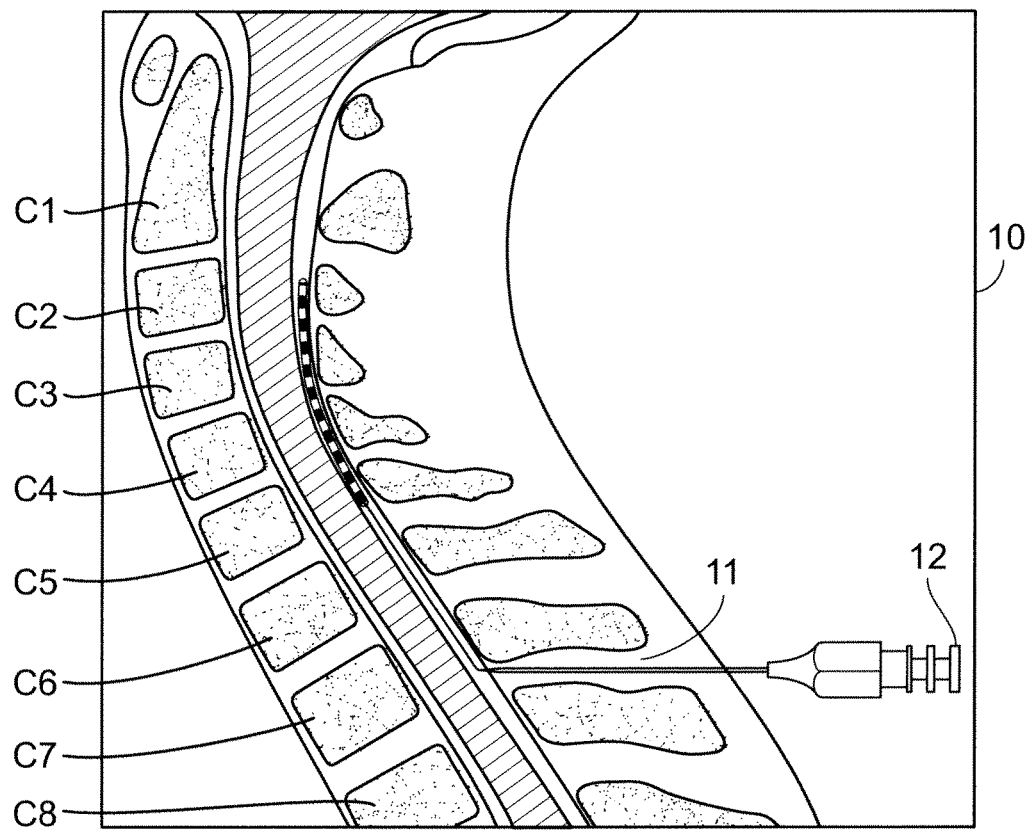
FIG. 1a is a partial sectional side view illustrating a percutaneous stimulation lead insertion technique for a purpose of stimulating the cervical spinal cord to prevent or treat arterial vasospasm.
Figure 2:
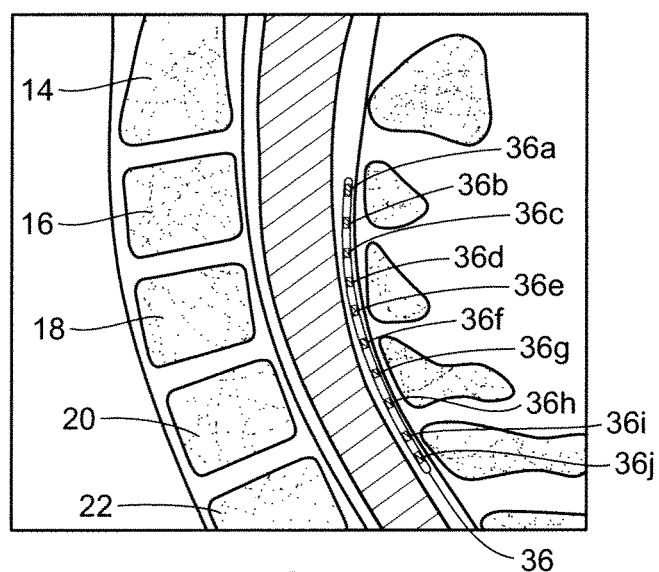
FIG. 2 is a partial sectional side view of a human body having a laminotomy stimulator lead positioned within the cervical spinal canal in accordance with the present invention.
Figure 3:
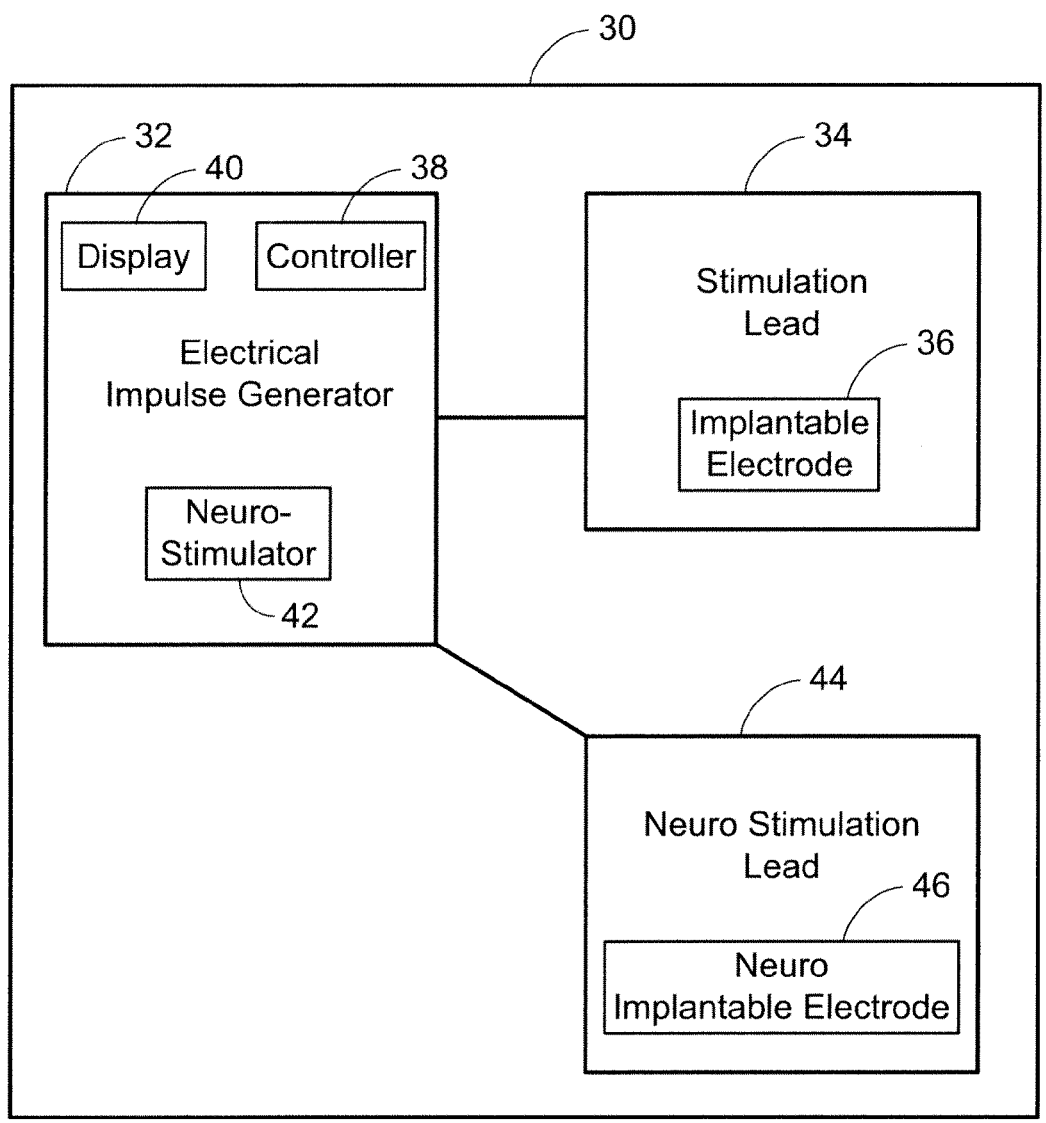
FIG. 3 is a schematic view of one embodiment of a spinal cord stimulator to practice the invention.

FIG. 3 is schematic view of one embodiment of a spinal cord stimulator 30 that can be used to practice the invention. FIG. 3 shows an electrical impulse generator 32. The electrical impulse generator 32 may incorporate a controller or any suitable processor 38. The electrical impulse generator 32 may be any suitable spinal cord stimulator that provides an electrical impulse to the spine. For example, electrical impulse generator 32 may comprise a single stimulation lead 34 or may comprise a plurality of stimulation leads. The electrical impulse generator 32 is operatively coupled to a stimulation lead 34 having an implantable electrode portion 36, wherein the electrical impulse generator 32 is arranged to deliver the predetermined electrical signal to the electrode portion 36.

The implantable electrode portion 36 may be any suitable electrode including: intravascular, transcutaneous, intracutaneous, patch-type, cuff-type, tape-type, screw-type, barb-type, metal, wire, balloon-type, basket-type, umbrella-type or suction-type electrodes. Guided or steerable catheter devices comprising electrodes may be used alone or in combination with the implantable electrode portion 36. For example, a catheter comprising one or more wire, metal strips or metal foil electrodes or electrode arrays may be inserted adjacent the spine. The implantable electrode portion 36 may be oriented in any fashion along the catheter device, including longitudinally or transversely. Various techniques such as ultrasound and fluoroscopy may be used to facilitate positioning of the electrodes.

All or a portion of the implantable electrode portion 36 may be placed in any suitable manner for providing stimulation to the spine. The stimulation lead 34 may be placed invasively or non-invasively. In one embodiment, all or a portion of the implantable electrode portion 36 is implanted adjacent the spine. Alternatively, all or a portion of the implantable electrode portion 36 is implanted adjacent specific vertebrae.

Figure 4:
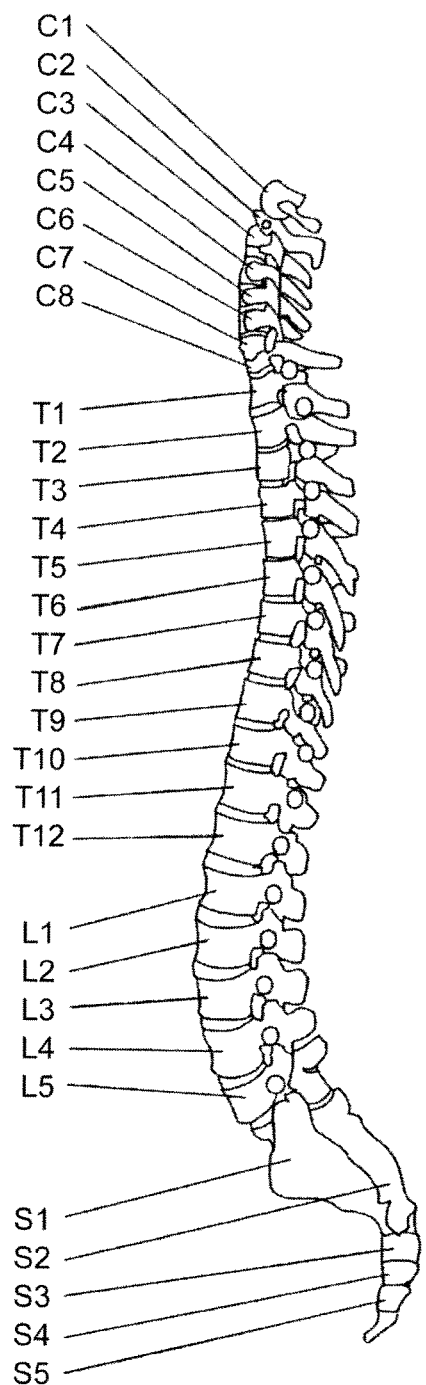
FIG. 4 is a cross sectional view of the spine

As set forth in FIG. 4, the spinal cord is divided into specific neurological segments. The cervical spinal cord is divided into eight levels (C1-C8) and contributes to different functions in the neck and arms.

In one embodiment, the implantable electrode portion 36 is implanted in the cervical spinal region at the C1-C3 level. In another embodiment, the implantable electrode portion 36 is implanted in the cervical spinal region at the C3-C5 level. In some embodiments, the implantable electrode portion 36 comprises a single contact so that electrical stimulation can be carried out on one specific area (or contact point) of the spinal cord. In some embodiments, the implantable electrode portion comprises multiple contacts (36a-36j) so that electrical stimulation can be carried out on more than one area (or contact points) of the spinal cord simultaneously or sequentially. For example, in some embodiments, a first group of contacts is disposed adjacent a first desired implant location adjacent an upper cervical spinal region of the subject and a second group of contacts is disposed adjacent a lower cervical spinal region of the subject and the electrical impulse generator 32 is activated to deliver the desired electrical signal to only the first group of contacts based on the presence of cerebral vasospasm and activating the electrical impulse generator 32 to deliver the electrical signal to only the second group of contacts based on the absence of cerebral vasospasm. In other embodiments, the electrical impulse generator 32 is activated to deliver the desired electrical signal to both the first and second groups of contacts. In one embodiment, electrical stimulation is carried out at both the C1-C3 and C3-C5 levels. Alternatively, the implantable electrode portion 36 is/are a guided or steerable electrode which allows its position to be adjusted during the medical procedure. Different electrode positions are accessible through various access openings along the spinal cord. The implantable electrode portion 36 may be positioned endoscopically through a percutaneous port, through an incision in the spine, placed on the skin or in combinations thereof. The present invention includes various electrodes, catheters and electrode catheters suitable for spinal cord stimulation.

In one embodiment of the present invention, the location of the implantable electrode portion 36 is chosen to elicit maximum stimulation to the spinal cord while preventing current spread to adjacent tissues. Furthermore, a non-conductive material such as plastic may be employed to sufficiently enclose the electrodes of all the configurations to shield them from the surrounding tissues and vessels, while exposing their confronting edges and surfaces for positive contact with the spinal cord, or the spinal cord coverings.

In some embodiments, the electrical impulse generator 32 incorporates a neuro stimulator 42. For example, FIG. 3 shows a nerve stimulation lead at 44. Electrodes used to stimulate a nerve such as the vagal nerve may be, for example, non-invasive, e.g., clips, or invasive, e.g., needles or probes. The application of an electrical stimulus to the right or left vagal nerve may include, but is not limited to bipolar and/or monopolar techniques. Different electrode positions are accessible through various access openings, for example, in the cervical or thorax regions. Nerve stimulation lead 44 may be positioned through a thoracotomy, sternotomy, endoscopically through a percutaneous port, through a stab wound or puncture, through a small incision in the neck or chest, through the internal jugular vein, the esophagus, the trachea, placed on the skin or in combinations thereof. Electrical stimulation may be carried out on the right vagal nerve, the left vagal nerve or to both nerves simultaneously or sequentially. The present invention may include various electrodes, catheters and electrode catheters suitable for vagal nerve stimulation to temporarily stop or slow the beating heart alone or in combination with other heart rate inhibiting agents.

Nerve stimulation implantable electrodes 46 may be endotracheal, endoesophageal, intravascular, transcutaneous, intracutaneous, patch-type, balloon-type, cuff-type, basket-type, umbrella-type, tape-type, screw-type, barb-type, metal, wire or suction-type electrodes. Guided or steerable catheter devices comprising electrodes may be used alone or in combination with the nerve stimulation implantable electrodes 46. For example, a catheter comprising one or more wire, metal strips or metal foil electrodes or electrode arrays may be inserted into the internal jugular vein to make electrical contact with the wall of the internal jugular vein, and thus stimulate the vagal nerve adjacent to the internal jugular vein. Access to the internal jugular vein may be via, for example, the right atrium, the right atrial appendage, the inferior vena cava or the superior vena cava. The catheter may comprise, for example, a balloon which may be inflated with air or liquid to press the electrodes firmly against the vessel wall. Similar techniques may be performed by insertion of a catheter-type device into the trachea or esophagus. Additionally, tracheal tubes and esophageal tubes comprising electrodes may be used.

Nerve implantable electrodes 46 may be oriented in any fashion along the catheter device, including longitudinally or transversely. Various techniques such as ultrasound, fluoroscopy and echocardiography may be used to facilitate positioning of the electrodes. If desired or necessary, avoidance of obstruction of blood flow may be achieved with notched catheter designs or with catheters which incorporate one or more tunnels or passageways.

In some embodiments, the spinal cord stimulation described herein is administered to a subject in need thereof for a period of time selected from the group consisting of 30 minutes, 1 hour, 2 hours, 3 hours, 4 hours, 6 hours, 8 hours, 12 hours, 24 hours, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or longer if warranted by the subject's condition.

The implantable electrode portion 36 may be in communication with a controller 38 as shown in FIG. 3. The controller 38 may thus be used to process the pulses being transmitted from the implantable electrode portion 36. The controller 38 may store information about the pulses being generated. The controller 38 may also be used to control or monitor the level or duration of spinal stimulation that occurs.

Electrical impulse generator 32 may incorporate one or more switches to facilitate regulation of the various components by the surgeon. One example of such a switch is a foot pedal. The switch may also be, for example, a hand switch, or a voice-activated switch comprising voice-recognition technologies. The switch may be incorporated in or on one of the surgeon's instruments, such as surgical site retractor, or any other location easily and quickly accessed by the surgeon.

Electrical impulse generator 32 may also include a display 40. Electrical impulse generator 32 may also include other means of indicating the status of various components to the surgeon such as a numerical display, gauges, a monitor display or audio feedback. Electrical impulse generator 32 may also include one or more visual and/or audible signals used to prepare a surgeon for the start or stop of spinal cord stimulation and/or cardiac stimulation.

Any commercially-available spinal cord stimulator can be used as the electrical impulse generator to practice the invention. In one embodiment, the electrical impulse generator 32 is a commercially-available neurostimulation device more commonly used for the management of chronic pain and include the SYNERGY, INTREL, RESTORE, RESTORE-ADVANCED, RESTORE-PRIME, PRIME-ADVANCED, RESTORE-ULTRA, X-TREL, and MATTRIX neurostimulation systems from Medtronic, Inc. The percutaneous leads and electrodes in this system are either quadripolar (4 contacts), such as the PISCES-QUAD, PISCES-QUAD PLUS and the PISCES-QUAD COMPACT, VERIFY, or octapolar (8 contacts) such as the OCTAD, OCTAD COMPACT and the OCTAD SUBCOMPACT lead-electrode system. The surgical leads themselves are quadripolar, such as the RESUME II Lead-electrode system, the RESUME TL Lead-electrode system and the ON-POINT PNS Lead-electrode system, or octapolar, such as the SPECIFY Lead-electrode system, the 2×4 HINGED Lead-electrode system, or hexadecimapolar (16 contacts), such as SPECIFY 5-6-5 Lead-electrode system, to create multiple stimulation combinations and a broad area of paresthesia. These neurostimulation systems and associated lead-electrode systems are described in U.S. Pat. Nos. 6,671,544; 6,654,642; 6,360,750; 6,353,762; 6,058,331; 5,342,409; 5,031,618 and 4,044,774, each of which is incorporated herein by reference. Other commercially available systems that may useful for the practice of this invention as described herein include the rechargeable PRECISION Spinal Cord Stimulation System (Advanced Bionics Corporation, Sylmar, Calif.; which is a Boston Scientific Company) which can drive up to 16 electrodes (see e.g., U.S. Pat. Nos. 6,735,474; 6,735,475; 6,659,968; 6,622,048; 6,516,227 and 6,052,624); the GENESIS, GENESIS XP, EON, EON MINI and RENEW Spinal Cord Stimulators available from Advanced Neuromodulation Systems, Inc. (Plano, Tex.; see e.g., U.S. Pat. Nos. 6,748,276; 6,609,031 and 5,938,690); and the Vagus Nerve Stimulation (VNS) Therapy System available from Cyberonics, Inc. (Houston, Tex.; see e.g., U.S. Pat. Nos. 6,721,603 and 5,330,515).

Electrical impulse generators may also be classified based on their source of power, which includes: battery powered, radio-frequency (RF) powered, or a combination of both types. For battery powered electrical impulse generators, an implanted, non-rechargeable or RF-recharged battery is usually used as the source of power. The battery, an optional RF-receiving coil and the leads with their electrodes are all surgically implanted and thus the electrolytic device, other than the optional transmitting coil, is completely internal. The settings of the totally implanted electrical impulse generator can be controlled by the patient through an external magnet. The lifetime of the implant, when powered by a non-rechargeable battery, is generally limited by the duration of battery life and ranges from two to four years depending upon usage and power requirements. For RF-powered electrical impulse generators, the radio-frequency is transmitted from an externally worn source to an implanted passive receiver, which charges usually an implanted rechargeable battery, but may optionally charge a capacitor, such as an electrochemical supercapacitor. Since the source of power for the transmitting coil can be the grid, or a readily rechargeable battery, or a replaceable non-rechargeable battery, the radio-frequency system provides greater power and can power electrodes generating electrochemically a greater amount or flux of the pain-relieving oxidant or its precursor; or it can power a greater number of oxidant generating electrodes; or it can power electrodes having a greater area at which more oxidant is generated. Specific earlier disclosed examples include an electrical impulse generator that has a battery power source contained within to supply power over an eight hour period in which power may be replenished by an external radio frequency coupled device (see, for example, U.S. Pat. No. 5,807,397, incorporated herein by reference) or an electrical impulse generator which is controlled by an external transmitter using data signals and powered by radio frequency (see, for example, U.S. Pat. No. 6,061,596, incorporated herein by reference).

In one embodiment, the electrical impulse generator generates an impulse frequency within the range of 2-3,000 Hz. In other embodiments, the impulse frequency generated is selected from the group consisting of 2, 5, 25, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000 Hz or more or any range therebetween.

The superior cervical ganglion serves as the most important source of sympathetic input to the brain. Although most of the ganglion is formed by branches of the first four cervical nerves, the sympathetic part is formed by preganglionic fibers that originate from the lateral column at the upper thoracic levels, leaving the spinal cord with the thoracic spinal nerves, traveling through the sympathetic chain until they reach the superior ganglion, where they synapse with postganglionic nerves [21]. Accompanying the internal carotid artery, the sympathetic nerves enter the skull. Because of the difference in growth rate between the spinal cord and the bony spine, the upper level of the thoracic spinal cord is located at the level of C7.

It seems quite clear that morphologic changes occur in the cerebral vessels after SAH, and the inflammatory response and local chemical agents are responsible for the induction of vasospasm [22]. The sympathetic system also plays an important role in the pathogenesis of this process [23,24]. Interestingly, this has been indirectly supported by Yasargil [24] who suggested separating the vessel wall from the adventitial sympathetic nerve plexus during the surgery for aneurysm repair.

Naredi et al. [25] found increased sympathetic activity in patients with nontraumatic SAH. The total body norepinephrine spillover into plasma was approximately 3 fold higher after 48 h compared to the control groups. Further supporting this explanation for vasospasm origin, the higher levels were present between the 7th and 10th days after bleeding right around the empirically observed peak incidence of vasospasm occurrence. The numbers returned to normal in approximately 6 months of follow up. Trying to decrease of influence by the environmental factors, one of the control groups was formed by patients under clinical investigation for refractory pain that underwent catheterization in the intensive care unit.

The effects of cervical sympathectomy on vasospasm were demonstrated by Faleiros et al. [26]. The authors submitted rabbits to SAH by injection of autologous blood into the cisterna magna. The diameter of the basilar artery after the hemorrhage was analyzed by angiography in animals with bilateral sympathectomy of the superior cervical ganglion alone, bilateral sympathectomy of the superior plus inferior cervical ganglion, and control groups.

The sympathectomy of the superior cervical ganglion seemed to protect the animals from vasospasm. Treggiari et al. [23] performed cervical sympathetic blockade to treat nine patients with clinical cerebral vasospasm confirmed by angiography. They observed improvement in cerebral perfusion in all angiograms after the blockade, even though the caliber of the vessels did not change. The authors attributed this to a decreased peripheral resistance. One patient died of complications of initial hemorrhage and other 2 died from consequences of severe vasospasm.

The main concern with the scientific explanation of the CBF augmentation with SCS is the lack of clear understanding of the mechanisms for vasospasm development and resolution. It is possible that more central, medullary mechanisms are responsible for immediate vasospasm after SAH [31] and for subsequent vasodilatation needed for vasospasm treatment. At the same time, pure sympathetic pathways that originate in lower cervical spinal cord or in the cervicothoracic junction and travel through the sympathetic ganglion to the cerebral vessels along the wall of the carotid arteries may be responsible for development of delayed vasospasm that results in major post-SAH morbidity.

The experimental and initial clinical data do support the idea that upper cervical SCS facilitates CBF in patients with vasospasm and improved outcome. Superior cervical sympathectomy, on the other hand, seems to prevent vasospasm from development. Clinical results of Takanashi and Shinonaga [19] suggest possible augmentation in CBF that may be used as treatment for vasospasm, and not as its prophylaxis, contrary to what is postulated in the title of their publication. Animal data seem to support this concept as well [11]. However, in order to prevent the delayed vasospasm, one needs to create functional sympathectomy, either by literally removing or blocking the sympathetic ganglia or by applying SCS to the lower segments of the cervical spinal cord.

Based on the thorough literature review, we hypothesize that in order to prevent the SAH-related delayed vasospasm, SCS should target the lower cervical segments, but once the vasospasm is present, the patient may receive additional benefit and possibly improve clinical outcome by CBF augmentation and treatment of the vasospasm by stimulation of the upper cervical spinal cord.

At this point it is difficult to say whether SCS interacts with the lateral column of the medulla at those parameters that are normally used for pain treatment, but due to the limited data it would be impossible to exclude this possibility.

Benefits of vasospasm prevention have not yet been established since there were no studies comparing results in patients at risk of vasospasm that received or did not receive SCS before the vasospasm starts. If this is turns to be true and poses no additional risk to the patient, dedicated placebo-controlled randomized clinical studies in humans will be required to prove our hypothesis. We suggest implanting longer electrode arrays that would cover both lower and upper cervical segments. Lower cervical SCS may then be used during the first 5-6 days after the SAH for true vasospasm prophylaxis and the additional 10-14 days of SCS to the upper cervical segments to treat vasospasm in those who develop it despite the prophylactic SCS application.

EXAMPLE 1

Cervical spinal cord stimulation after acute aneurvsmal subarachnoid hemorrhage. The following Example establishes the feasibility and safety of prolonged cervical spinal cord stimulation (SCS) in the setting of acute aneurysmal subarachnoid hemorrhage (aSAH), as well as to evaluate clinical effects of cervical SCS in a small group of selected aSAH patients. The study was undertaken in preparation for a larger scale randomized trial of SCS for prevention of cerebral arterial vasospasm following aSAH.

Material and methods: A single arm non-randomized prospective study of cervical SCS in aSAH patients was performed in University of Illinois at Chicago. Standard percutaneous 8-contact SCS electrodes were implanted under an Investigational Device Exemption protocol in 12 consecutive patients that satisfied the following inclusion criteria: (1) age 18-65, (2) angiography-confirmed aSAH within 3 days prior to the electrode implantation, (3) Hunt/Hess (H&H) grade 2-4, (4) Fischer grade 2-4, (5) no history of previous cervical spine surgery, and (6) ability to obtain informed consent from the patient or family. All electrodes were inserted using percutaneous approach under general anesthesia immediately upon completion of the definitive surgical or endovascular procedure to secure the ruptured aneurysm. SCS was then delivered for the soonest of either 14 consecutive days or until the patient's discharge. Daily vital signs, laboratory values, transcranial Doppler, computed tomography and angiography results were recorded along with the information on presence of clinical vasospasm and all interventions aimed at vasospasm prevention and treatment.

Results: Mean age of implanted patients was 49 years (range—27-62), average H&H grade—2.9, average Fisher grade—3.3. Three had aneurysms coiled and 9—clipped. One patient developed multisystem failure and expired on post-operative day 11. In two patients, electrode was inadvertently pulled out on days 7 and 13 after the implantation. There were no complications related to the electrode insertion or to SCS during the entire study period. The angiographic vasospasm was observed in 6 out of 12 patients, and clinical vasospasm—in 2 out of 12; no patient suffered any vasospasm-related neurological complication. Both incidences were smaller than predicted based on the patients' Fisher and H&H grades.

Conclusion: The data presented herein demonstrates that cervical spinal stimulation is both a safe and feasible approach for treatment. Our data indicate that despite high level of acuity in patients after aSAH, general severity of medical condition, impaired level of consciousness, frequent patient re-positioning, need in multiple tests and variety of monitors, SCS electrodes may be safely implanted and maintained for the two-week period.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

Literature Cited:

[1] Fisher C M, Kistler J P, Davis J M. Relation of cerebral vasospasm to subarachnoid hemorrhage visualized by computerized tomographic scanning. Neurosurgery 1980; 6:1-9.

[2] Frontera J A, Claassen J, Schmidt J M, Wartenberg K E, Temes R, Connolly Jr E S, et al. Prediction of symptomatic vasospasm after subarachnoid hemorrhage: the modified fisher scale. Neurosurgery 2006; 59:21-7.

[3] Mocco J, Zacharia B, Komotar R, Connolly J R E S. A review of current and future medical therapies for cerebral vasospasm following aneurismal subarachnoid hemorrhage. Neurosurg Focus 2006; 21(3):E9.

[4] Doberstein C, Martin N A. Cerebral blood flow in clinical neurosurgery. In: Youmans J R, editor. Neurological surgery, 4th ed. Philadelphia: WB Saunders; 1996. p. 519-69.

[5] Slavin K. Epidural spinal cord stimulation: indications and technique. In: Schulder M, editor. Handbook of functional and stereotactic surgery. New York: Marcel Dekker; 2002. p. 417-30.

[6] Burchiel K J, Slavin K V. Peripheral neuropathic pain syndromes. In: Batjer H H, Loftus C M, editors. Textbook of neurological surgery. Philadelphia: LWW; 2003. p. 3013-22.

[7] Ebel H, Schomacker K, Balogh A, Volz M, Funke J, Schicha H, Klug N. High cervical spinal cord stimulation (CSCS) increases regional cerebral blood flow after induced subarachnoid haemorrhage in rats. Minim Invasive Neurosurg 2001; 44:167-71.

[8] Gurelik M, Kayabas M, Karadag O, Goksel H M, Akyuz A, Topaktas S. Cervical spinal cord stimulation improves neurological dysfunction induced by cerebral vasospasm. Neuroscience 2005; 134:827-32.

[9] Isono M, Kaga A, Fujiki M, Mori T, Hori S. Effect of spinal cord stimulation on cerebral blood flow in cats. Stereotact Funct Neurosurg 1995; 64:40-6.

[10] Lee J Y, Huang D L, Keep R, Sagher O. Effect of electrical stimulation of the cervical spinal cord on blood flow following subarachnoid hemorrhage. J Neurosurg 2008; 109: 1148-54.

[11] Patel S, Huang D L, Sagher O. Sympathetic mechanisms in cerebral blood flow alterations induced by spinal cord stimulation. J Neurosurg 2003; 99:754-61.

[12] Patel S, Huang D L, Sagher O. Evidence for a central pathway in the cerebrovascular effects of spinal cord stimulation. Neurosurgery 2004; 55: 201-6.

[13] Sagher O, Huang D L. Effects of cervical spinal cord stimulation on cerebral blood flow in the rat. J Neurosurg 2000; 93(Suppl. 1):71-6.

[14] Yang X, Farber J P, Wu M, Foreman R D, Qin C. Roles of dorsal column pathway and transient receptor potential vanilloid type 1 in augmentation of cerebral blood flow by upper cervical spinal cord stimulation in rats. Neuroscience 2008; 152:950-8.

[15] Vincenzo S, Kyventidis T. Epidural spinal cord stimulation in lower limb ischemia. Acta Neurochir (Suppl.) 2007; 97(Pt. 1):253-8.

[16] Clavo B, Robaina F, Catala L, Valcarcel B, Morera J, Carames M A, et al. Increased locoregional blood flow in brain tumors after cervical spinal cord stimulation. J Neurosurg 2003; 98:1263-70.

[17] Hosobuchi Y. Treatment of cerebral ischemia with electrical stimulation of the cervical spinal cord. Pacing Clin Electrophysiol 1991; 14:122-6.

[18] Robaina F, Clavo B. Spinal cord stimulation in the treatment of post-stroke patients: current state and future directions. Acta Neurochir 2007; 97(Pt. 1):277-82.

[19] Takanashi Y, Shinonaga M. Spinal cord stimulation for cerebral vasospasm as prophylaxis. Neurol Med Chir (Tokyo) 2000; 40:352-6.

[20] Upadhyaya C D, Sagher O. Cervical spinal cord stimulation in cerebral ischemia. Acta Neurochir (Suppl.) 2007; 97(Pt. 1):267-75.

[21] Truex R C, Carpenter M B. Strong and Elwyn's human neuroanatomy. Baltimore: Williams & Wilkins; 1964. p. 240-42.

[22] Macdonald R L, Weir B. Pathology and pathogenesis. In: Macdonald R L, Weir B, editors. Cerebral vasospasm, San Diego: Academic Press; 2001. p. 87-174.

[23] Treggiari M M, Romand J A, Martin J B, Reverdin A, Rüfenacht D A, de Tribolet N. Cervical sympathetic block to reverse delayed ischemic neurological deficits after aneurysmal subarachnoid hemorrhage. Stroke 2003; 34:961-7.

[24] Yasargil M G. Microneurosurgery, vol. 1. Stuttgart: Thieme; 1984. p. 271.

[25] Naredi S, Lambert G, Ede'n E, Zall S, Runnerstam M, Rydenhag B, Friberg P. Increased sympathetic nervous activity in patients with nontraumatic subarachnoid hemorrhage. Stroke 2000; 31:901-6.

[26] Faleiros A, Maffei F H, Resende L A. Effects of cervical sympathectomy on vasospasm induced by meningeal haemorrhage in rabbits. Arq Neuropsiquiatr 2006; 64:572-4.

[27] Visocchi M. Spinal cord stimulation and cerebral haemodynamics. Acta Neurochir (Suppl.) 2006; 99:111-6.

[28] Visocchi M, Cioni B, Vergari S, Marano G, Pentimalli L, Meglio M. Spinal cord stimulation and cerebral blood flow: an experimental study. Stereotact Funct Neurosurg 1994; 62:186-90.

[29] Visocchi M, Argiolas L, Meglio M, Cioni B, Basso P D, Rollo M, et al. Spinal cord stimulation and early experimental cerebral spasm: the "functional monitoring" and the "preventing effect". Acta Neurochir (Wien) 2001; 143:177-85.

[30] Hosobuchi Y. Electrical stimulation of the cervical spinal cord increases cerebral blood flow in humans. Appl Neurophysiol 1985; 48:372-6.

[31] Cetas J S, Lee D, Alkayed N, Heinricher M M. Coupled control of pain and cerebral blood flow in the medulla. In: New horizons in functional neurosurgery, Program of 2008 ASSFN meeting, Vancouver, BC, 2008. p. 81.

What is claimed is:

1. A method of preventing cerebral vasospasm in a subject having had a subarachnoid hemorrhage, the method comprising
    providing an electrical impulse generator capable of generating a predetermined electrical signal, wherein the electrical impulse generator is operatively coupled to a stimulation lead having an implantable electrode portion, wherein the electrical impulse generator is arranged to deliver the predetermined electrical signal to the electrode portion;
    selecting an implant location in vertebrae C3-C5 of a lower cervical spinal region;
    surgically implanting the stimulation lead in the lower cervical spinal region and positioning the electrode portion of the stimulation lead in an area adjacent to the implant location with the electrode portion disposed behind the spinal cord in the lower cervical spinal region, such that the stimulation lead is positioned to deliver the predetermined electrical signal from the electrical impulse generator to the selected implant location; and
    activating the electrical impulse generator for a predetermined period of time to generate the predetermined electrical signal to prevent cerebral vasospasm in the subject.

2. The method of claim 1, comprising performing a partial laminectomy and implanting the stimulation lead through the partial laminectomy.

3. The method of claim 1, comprising performing a partial removal of ligamentum flavum at a removal location and implanting the stimulation lead through the removal location.

4. The method of claim 1, comprising arranging the electrical impulse generator to cause the predetermined electrical signal to have an impulse frequency within the range of 5-3,000 Hz.

5. A method of treating cerebral vasospasm in a subject having had a subarachnoid hemorrhage, the method comprising
    providing an electrical impulse generator capable of generating a predetermined electrical signal, wherein the electrical impulse generator is operatively coupled to a stimulation lead having an implantable electrode portion, wherein the connector the electrical impulse generator is arranged to deliver the predetermined electrical signal to the electrode portion;
    selecting an implant location in vertebrae C1-C3 of an upper cervical spinal region;
    surgically implanting the stimulation lead in the upper cervical spinal region and positioning the electrode portion of the stimulation lead in an area adjacent to the implant location and positioning the electrode portion behind the spinal cord in the upper cervical spinal region, such that the stimulation lead is positioned to deliver the predetermined electrical signal from the electrical impulse generator to the selected implant region; and
    activating the electrical impulse generator for a predetermined period of time to generate the predetermined electrical signal to treat cerebral vasospasm in the subject.

6. The method of claim 5, comprising performing a partial laminectomy and implanting the stimulation lead through the partial laminectomy.

7. The method of claim 5, comprising performing a partial removal of ligamentum flavum at a removal location and implanting the stimulation lead through the removal location.

8. The method of claim 5, comprising arranging the electrical impulse generator to cause the predetermined electrical signal to have an impulse frequency within the range of 5-3,000 Hz.

9. A method of applying spinal cord stimulation in a subject having had a subarachnoid hemorrhage, the method comprising
    providing an electrical impulse generator capable of generating a predetermined electrical signal, wherein the electrical impulse generator is operatively coupled to a stimulation lead having an implantable electrode portion, wherein the connector the electrical impulse generator is arranged to direct the predetermined electrical signal toward the electrode portion;
    assessing whether the subject has a presence of a cerebral vasospasm or an absence of a cerebral vasospasm;
    selecting a first implant location in vertebrae C1-C3 of an upper cervical spinal region based on the presence of cerebral vasospasm, and selecting a second implant location in vertebrae C3-C5 of a lower cervical spinal region based on the absence of cerebral vasospasm;
    surgically implanting the stimulation lead and positioning the electrode portion of the stimulation lead in an area behind the spinal cord adjacent the selected first or second implant location, such that the stimulation lead is positioned to deliver the predetermined electrical signal from the electrical impulse generator to the selected first or second implant location; and
    activating the electrical impulse generator for a predetermined period of time to generate the predetermined electrical signal to treat or prevent cerebral vasospasm in the subject.

10. The method of claim 9, comprising performing a partial laminectomy and implanting the stimulation lead through the partial laminectomy.

11. The method of claim 9, comprising performing a partial removal of ligamentum flavum at a removal location and implanting the stimulation lead through the removal location.

12. The method of claim 9, comprising arranging the electrical impulse generator to cause the predetermined electrical signal to have an impulse frequency within the range of 5-3,000 Hz.

13. A method of applying spinal cord stimulation in a subject having had a subarachnoid hemorrhage, the method comprising
- providing an electrical impulse generator capable of generating a desired electrical signal, the electrical impulse generator operatively coupled to an implantable electrode and arranged to send the desired electrical signal toward the electrode;
- providing the electrode with a plurality of contacts, including a first group of contacts and a second group of contacts;
- assessing whether the subject has a presence or an absence of a cerebral vasospasm;
- implanting the electrode in a selected area of the spine with the first group of contacts disposed in a first desired location in vertebrae C1-C3 of an upper cervical spinal region of the subject, and with the second group of contacts disposed in vertebrae C3-C5 of a lower cervical spinal region of the subject;
- activating the electrical impulse generator to deliver the desired electrical signal to only the first group of contacts based on the presence of cerebral vasospasm and activating the electrical impulse generator to deliver the electrical signal to only the second group of contacts based on the absence of cerebral vasospasm.

14. The method of claim 13, comprising activating the electrical impulse generator to deliver the desired electrical signal to both the first and second groups of contacts.

* * * * *